US010586613B2

(12) United States Patent
Kogan et al.

(10) Patent No.: US 10,586,613 B2
(45) Date of Patent: Mar. 10, 2020

(54) SYSTEM AND METHOD FOR GENERATING MEDICAL SERVICE PROVIDER INFORMATION INCORPORATING REFERRAL PATTERN DATA

(71) Applicant: MDX Medical, Inc., Lyndhurst, NJ (US)

(72) Inventors: Daniel Kogan, Brooklyn, NY (US); Erika Boyer, Morganville, NJ (US)

(73) Assignee: MDX Medical, Inc., Lyndhurst, NJ (US)

( * ) Notice: Subject to any disclaimer, the term of this patent is extended or adjusted under 35 U.S.C. 154(b) by 818 days.

(21) Appl. No.: 14/300,802

(22) Filed: Jun. 10, 2014

(65) Prior Publication Data

US 2015/0356248 A1    Dec. 10, 2015

(51) Int. Cl.
*G16H 10/60*     (2018.01)
*G16H 40/20*     (2018.01)
*G06Q 30/02*     (2012.01)
*G06Q 50/24*     (2012.01)
*G06Q 50/22*     (2018.01)

(52) U.S. Cl.
CPC .......... *G16H 10/60* (2018.01); *G06Q 30/0282* (2013.01); *G06Q 50/22* (2013.01); *G06Q 50/24* (2013.01); *G16H 40/20* (2018.01)

(58) Field of Classification Search
CPC .... G06F 19/322; G06F 19/327; G06F 19/324; G06F 19/326; G06Q 30/0282; G06Q 30/02; G16H 10/60
USPC ............................................................ 705/2
See application file for complete search history.

(56) References Cited

U.S. PATENT DOCUMENTS

| 2003/0163349 | A1* | 8/2003 | Ho ......................... | G06Q 50/22 |
| | | | | 705/2 |
| 2007/0288502 | A1* | 12/2007 | Silverthorne ..... | G06F 17/30241 |
| 2008/0010087 | A1* | 1/2008 | Daniel ................... | G06Q 40/08 |
| | | | | 705/2 |
| 2014/0052569 | A1* | 2/2014 | Yoo ........................ | G06Q 10/06 |
| | | | | 705/26.7 |

* cited by examiner

*Primary Examiner* — Hiep V Nguyen
(74) *Attorney, Agent, or Firm* — Leydig, Voit & Mayer, Ltd.

(57) ABSTRACT

A system is described for rendering medical service provider entity information. The system is configured to identify a medical service provider entity for which referrals data enhanced medical service provider information will be rendered for presentation to a requesting user. The a medical service provider referral processing engine accesses medical service provider referral information relating to the medical service provider entity, wherein the referral information specifies a value representing referrals received by the medical service provider entity. The referral processing engine transforms the referral information to render a received referrals value, wherein the transformation comprises at least summing a plurality of referral values corresponding to referrals received by the medical service provider entity. The referrals value is incorporated with medical service provider information to render referrals data enhanced medical service provider information.

20 Claims, 3 Drawing Sheets

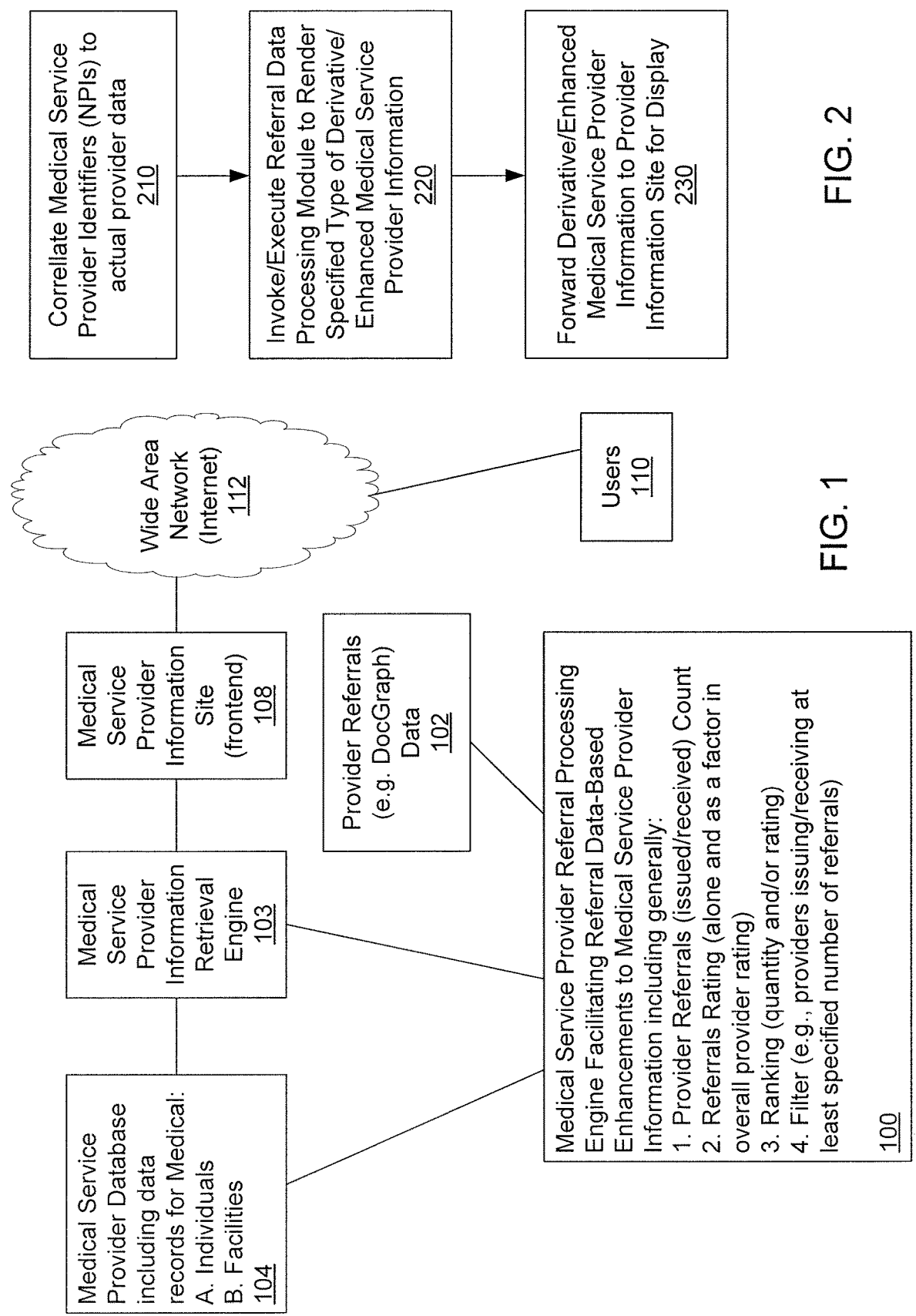

| 302 | Referrals Issued by Provider |
|---|---|
| 304 | Referrals Received by Provider |
| 306 | Specialties |
| 310 | Geographic Areas |
| 320 | Referrals Score |
| 322 | Referral Rankings |
| 324 | Unique Provider Connections |
| 326 | Unique Geographic Connections |
| 328 | Trusted Circle of Providers (Graphically Depicted in FIG. 4) |

FIG. 3

SYSTEM AND METHOD FOR GENERATING MEDICAL SERVICE PROVIDER INFORMATION INCORPORATING REFERRAL PATTERN DATA

FIELD OF THE INVENTION

This invention relates generally to the field of medical service provider databases. More particularly, the invention is directed to medical service provider information services that render listings of candidate medical service providers, and related information, based upon submitted requests specifying desired traits/characteristics for medical service providers.

BACKGROUND OF THE INVENTION

In recent years there has been a proliferation of searchable data available to the general public via the Internet. The area of medical service providers is no exception. Today, users can go on line and submit search requests relating to a wide variety of medical services, and receive a variety of information. A user can access a medical service provider search site and enter a variety of search parameter values including, for example: a medical service provider type, a geographic region, and a variety of personal preferences. A retrieval engine operating in association with the search site applies search parameter values specified by the user to a database comprising information for a population of medical service providers represented by data record contents of a medical service provider database. An example of one such medical service provider database and retrieval engine is described in Rothschild et al., U.S. Pat. No. 8,694,441, entitled "Method for Determining the Quality of a Professional."

People generally place a high degree of value on their health. When a person consults a medical service provider search site for listing of service providers for diagnosing and/or treating a particular type of ailment, it is important that the provided information instill a high level of confidence that a medical service provider selected from the rendered information can meet particularized needs and/or expectations of the patient. Thus, when a patient consults a particular medical service provider identified in ranked results provided by a search site, it is important that the actual visit experience meets the user's expectations created by the provided information—especially if the selected service provider was identified as a best match for the particular patient based upon the particularized search parameter values submitted by the user.

A number of challenges are faced by medical service provider search sites with regard to providing results that match patient expectations. One challenge is to acquire sufficient amounts of information; both type and quantity, about medical service providers to ensure sufficient granularity/precision with regard to defining desired service provider candidates. Another challenge is to ensure the information relied upon to render ranked match results accurately characterizes the skills, traits and reputations of subject service providers.

For purely objective criteria, finding and ranking matches is straight-forward. For example, a request for ranked search results for a service provider closest to a specified location is very straight-forward and easy to confirm. Moreover, it is highly likely that a patient's expectations will be met in cases where provided information pertains to purely objective criteria. However, selecting a doctor is rarely, if ever, a purely objective determination.

A substantial challenge, when providing requested medical service provider information, exists with respect to providing medical service provider information meeting subjective expectations of requestors. Known medical service provider information sources (e.g. retrieval engines and information sites) support a variety of objective factors that operate as proxies for subjective evaluations and identification of desired individual medical service providers for particular patient needs. However, actual subjective evaluations of medical service providers arise from a combination of factors that cannot possibly be acquired and maintained in any reasonably sized database.

User satisfaction with medical service provider information acquired in response to user-submitted requests is closely tied to the ability of the information provider to render provider information that closely aligns with user expectations created by the provided information (e.g., provider ratings and quality descriptions). It is readily apparent that designers of a medical service provider information source/site face significant challenges when designing and implementing the medical service provider information source/site that meets subjective expectations of users. However, such challenges must be overcome since, the value, utility, and ultimately the continued existence of such information sources/sites is inextricably linked to actual user experience meeting expectations created by the provided search results.

To that end, a medical service provider information source/site needs to draw from and expose a broad set of provider description/definition/evaluation parameter types to instill confidence in users that the medical service provider information source/site can render requested information meeting subjective needs and expectations of individual users.

SUMMARY OF THE INVENTION

Embodiments of the invention are used to provide a system and method for rendering requested medical service provider entity information via a medical service provider information retrieval engine. The retrieval engine is configured to access information stored in a medical service provider database containing information relating to service provider entities. The system is configured by computer-executable instructions to carry out a method. The method includes identifying a medical service provider entity for which referrals data enhanced medical service provider information will be rendered for presentation to a requesting user. The method further includes accessing, by a medical service provider referral processing engine, medical service provider referral information relating to the medical service provider entity, wherein the referral information specifies a value representing referrals received by the medical service provider entity. The referral processing engine performs a transformation on the medical service provider referral information obtained during the accessing to render a provider entity received referrals value, wherein the transformation comprises at least summing a plurality of referral values corresponding to referrals received by the medical service provider entity. The provider entity received referrals value is incorporated with medical service provider information obtained by the retrieval engine to render referrals data enhanced medical service provider information.

BRIEF DESCRIPTION OF THE DRAWINGS

While the appended claims set forth the features of the present invention with particularity, the invention and its advantages are best understood from the following detailed description taken in conjunction with the accompanying drawings, of which:

FIG. 1 is a schematic diagram illustrating a networked environment wherein a medical service provider referral processing engine is provided to render a variety of basic and derivative referral data via a medical service provider information site (including a medical service provider retrieval engine front-end user interface, the information provided via the provider information site being enhanced by incorporating provider-to-provider (inferred and/or actual) referral data;

FIG. 2 is a flowchart summarizing operations performed to render enhanced referral data from basic referral data and provider information acquired from a provider database;

FIG. 3 is a list identifying various computer modules (identified by type) incorporated into the Medical service provider referral processing engine to render various types of provider referral data-enhanced provider information incorporated into listings and rankings provided via the medical service provider information site.

DETAILED DESCRIPTION OF THE DRAWINGS

Figure 4:
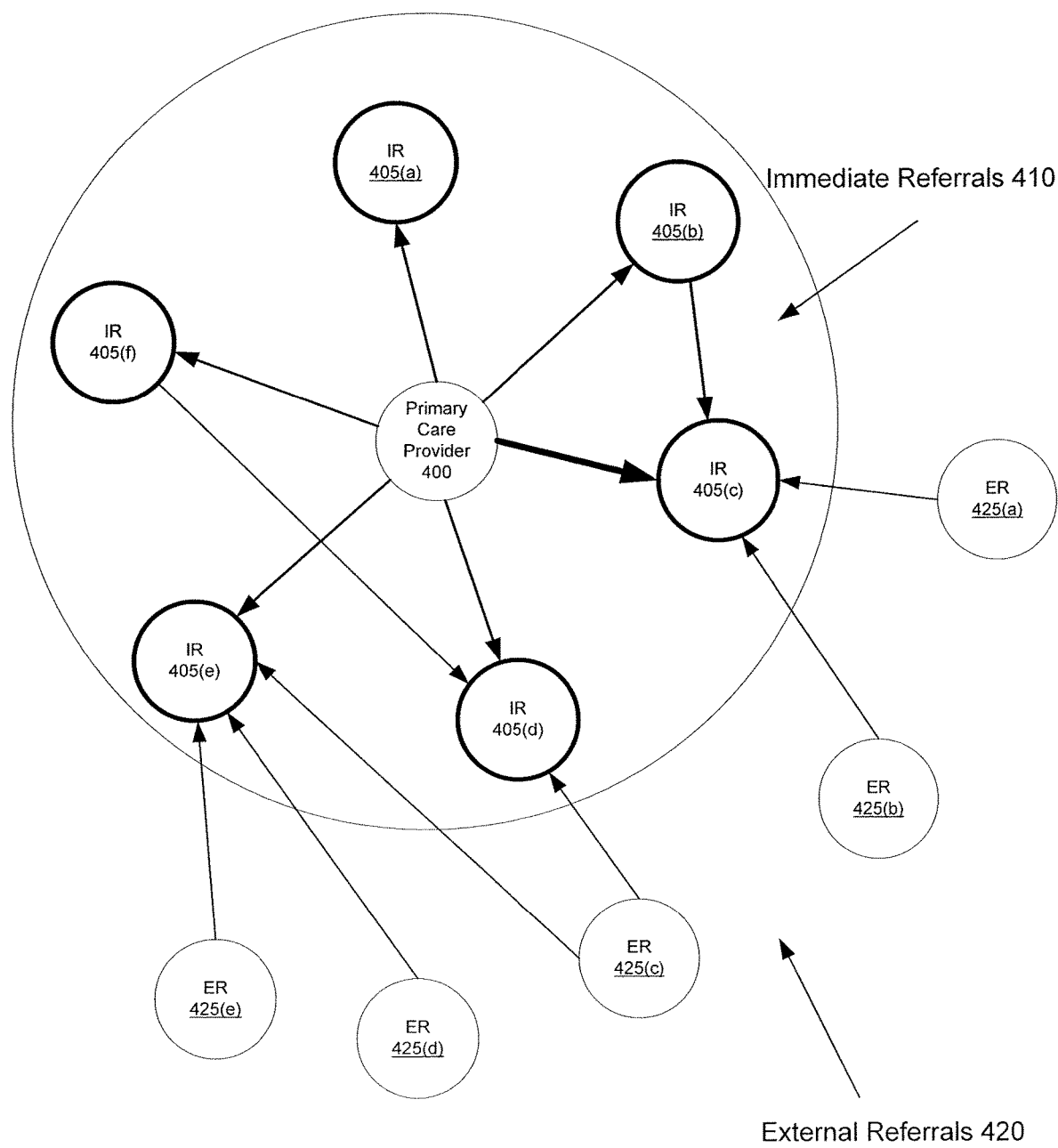
FIG. 4 illustratively depicts an exemplary set of referring-to-referred provider connections between identified doctors of the "trusted circle of providers" type of computer program module identified in FIG. 2.

The figures and associated written description provide illustrative examples of medical service provider information sources accessed via a medical service provider information site. The rendered information relating to identified medical service providers is selectively enhanced by applying referral data, which may correspond to actual and/or inferred referrals, to provider information for presentation to requesting users.

Turning to FIG. 1, a schematic diagram depicts functional/structural components of an exemplary networked system suitable for carrying out embodiments of the system and method described herein for rendering requested information. Such information is based upon both: (1) medical service provider data stored as records in tables of a database accessed by a medical service provider information retrieval engine invoked via a medical service provider information site, and (2) aggregated medical provider referral data. The elements depicted in FIG. 1 comprise programmed processes communicatively coupled (in many potential ways) and configured on programmed processors configured to execute computer-executable instructions stored on a computer-readable medium (e.g. a non-transitory computer-readable medium). Unless expressly stated (e.g. wide area network 112), connections between identified components depicted in FIG. 1 can be one, or a combination of more than one, physical (e.g. network interfaces) and/or logical (e.g. program interfaces) connections that facilitate the transfer of requests for information and corresponding rendered results between the identified components.

Continuing with the description of FIG. 1, the system includes a medical service provider referral processing engine 100 that comprises a set of modules stored on a non-transitory computer-readable medium including computer-executable instructions. The referral processing engine 100 carries out operations for incorporating referral pattern data into medical service provider information, based upon medical service provider referral data 102 (comprising actual and/or inferred referral counts) and, potentially, service provider data acquired, by a medical service provider information retrieval engine 103, from a medical service provider database 104. More particularly, the referrals processing engine 100 executes functions (processes, instances of which are executed by a programmed processor configured to carry out the functionality of the referral processing engine 100) to render a particular types of enhancements to the provider data retrieved by the provider information retrieval engine 103 from the provider database 104.

By way of example, the medical service provider information retrieval engine 103 includes a retrieval engine for obtaining a listing of provider entities in response to user-defined queries submitted via a medical service provider information site 108. In the context of retrieval engine results, the aforementioned enhancements include rendering accumulated medical service provider referrals data, tabulated from the medical service provider referral data 102 (e.g. inferred referrals from the DocGraph database comprising a compilation of tens of millions of records derived from Medicare patient visits to identified providers), for attachment to a set of providers identified in search results obtained by the medical service provider information retrieval engine 103. Examples of the accumulated referrals data include received actual/inferred referrals for a particular provider entity (e.g. individual, practice group, identifiable group including a set of identified individuals, etc.) and issued actual/inferred referrals for a particular provider entity (e.g. individual, practice group, group of identified individuals).

Another enhancement facilitated by the referral processing engine 100 is the rendering of a referral rating for an identified provider entity (e.g. doctor, practice group, hospital department, etc.). By way of example the medical service provider referral data 102 is analyzed (e.g., quantity of referrals and ratings of the providers that issued referrals received by the rated identified provider entity) to specify a comparative referral rating for the rated entity. Such rating can be provided as a single value used alone or alternatively as a factor for generating an overall rating to a particular medical services provider.

Another enhancement facilitated by the referral processing engine 100 is the ranking of a set of identified individuals or group provider entities. In illustrative examples, the medical service provider referral data 102 is applied to a listing of providers returned by a retrieval engine (or any other list source) to generate a ranking of relative referral strength for ones of the listed providers. By combining the referrals data with the search capabilities of the retrieval engine 103, the described system facilitates creating a ranking, and the ranking may include: (1) computing grouped rankings (e.g. quartiles), (2) specifying specialties, and (3) placing geographic limitations on retrieved medical service providers (e.g. national, city, state, zip, etc.). Such ranking can occur on an individual provider basis (e.g., the total, possibly weighted, referrals received) or on an identified group (e.g. referrals received by a group of providers identified as being affiliated with a particular hospital and having a particular area of practice/expertise). The actual generation of the ranking, based upon information extracted from medical service provider referral data 102, can occur in any of a variety of programmed processors/components.

Yet another enhancement facilitated by the referral processing engine 100 is the filtering of provider entities identified on a listing of medical service providers. In other examples of the general functionality of the functions/modules enumerated in FIG. 3, the referral information extracted by the medical service provider referral processing engine 100 is used to filter candidates provided in an initial listing of medical service provider entities. The filtering operation can be used, for example, to render an initial set of medical service provider entities for which additional data is acquired by the information retrieval engine 103 from the medical service provider database 104. The functionality of the referrals processing engine 100 is described further herein below with reference to FIGS. 2-4.

By way of example, the medical service provider referral data 102, which may comprise information relating to actual or inferred referrals, comprises a set of referral records provided by the known "DocGraph" database comprising a compilation of tens of millions of records derived from Medicare patient visits to identified providers. Each referral record comprises three fields: (1) a referring provider identification, (2) a referred provider identification, and (3) a quantity representing a total count of referrals (either actual or inferred) attributed to the identified combination of referring and referred providers. The medical service providers are identified by National Provider Identifiers (NPIs) that uniquely identify medical providers in the United States of America.

Regarding the content of the "quantity" field of the DocGraph records, the DocGraph referral data is aggregated and compiled on a yearly basis and a referral count is accumulated on a yearly basis. Thus, the value in the quantity field, of an instance of the DocGraph referral records, identifies the number of inferred referrals from an identified referring medical service provider to an identified referred medical service provider within an identified year.

In the illustrative example, the "referral" data obtained from the DocGraph referral database constitutes "inferred" referrals, wherein each instance of a referral is based upon a sequence of a same patient visiting first and second distinct identified medical service providers within a specified period (e.g., 1 month/30 days). The first provider visited in time is identified as the "referring" provider and the second provider visited sequentially thereafter in time is identified as the "referred" provider. Alternatively or additionally, the referral data includes actual referral data corresponding to an explicit recommendation provided by a referring provider, to a patient, to seek medical services from a specific medical services provider for diagnosis and/or treatment of a medical condition. Thus, it is contemplated that various alternative examples of the described system and method will use a variety of sources of actual referrals and/or inferred referrals information.

Continuing with the discussion of FIG. 1 and also referring to the flowchart depicted in FIG. 2, the medical service provider referral engine 100 performs two general types of operations. During 210, the medical service provider referral processing engine 100 correlates NPIs provided in the medical service provider referral data 102 information to detailed information about medical service providers maintained in the medical service provider database 104. By way of example, the provider information acquired for particular identified medical service providers includes: area of practice, specialty, expertise, geographic location, group affiliation, awards won, quality of education, affiliated hospitals (and corresponding rankings), patient ratings as well as specific attributes associated with the ratings, and a quality score. Furthermore, the medical service provider referral data 102 is combined with Medicare cost data to correlate such costs with providers and their affiliated hospitals to render distributions of Medicare costs as a function of hospital referrals.

During 220, based upon a derivative information request type, the referral processing engine 100 and/or the medical service provider information retrieval engine 103 invoke/execute computer-executable instructions stored on a non-transitory computer-readable medium to carry out functionality provided by one or more operation-specific modules (see e.g. FIG. 3) to render 'referral data-enhanced' medical service provider information retrieved by the medical service provider information retrieval engine 103 from the medical service provider database 104. The functionality of the referral processing engine 100 and information retrieval engine 103, using the medical service provider referral data 102 to enhance the information rendering functionality of the information retrieval engine 103, is described herein below with reference to FIGS. 3-4.

During 230, the referral data-enhanced medical service provider information is passed to the medical service provider information site 108 for presentation of the referral data-enhanced (derivative) medical service provider information to requesting users (e.g. users 110), An example of the medical service provider database 104, medical service provider information retrieval engine, and medical service provider information site 108 is described in Rothschild et al., U.S. Pat. No. 8,694,441, entitled "Method for Determining the Quality of a Professional."

The medical service provider information site 108, such as the one described in Rothschild, U.S. Pat. No. 8,694,441, includes a medical service provider search page. The medical service provider search page includes a set of search fields through which users 110 specify and submit search queries. The users 110 access the information site 108 via a wide area network 112. The search queries, specified via the search site, are executed by a medical service provider information retrieval engine 103 configured to access the contents of the medical service provider database 104 and retrieve medical service provider information corresponding to specified search parameters. The retrieved results of such searches executed by the information retrieval engine 103 are enhanced by the medical service provider referral processing engine 100 that accesses referral data, from the medical service provider referral data 102, relating to medical service providers identified in the search results. The retrieved information from the medical service provider database 104, enhanced by referrals information, is provided to the users 110 via the information site 108. Thus, in general, the medical service provider referral processing engine 100 operates as a source of additional medical service provider information, which may be attached with or incorporated into existing medical service provider information, that may be considered probative of the quality of service rendered by medical service providers enumerated in a listing of medical service providers acquired by the information retrieval engine 103 from the medical service provider database 104.

Turning to FIG. 3, an exemplary, extensible list of computer-modules configured on the medical service provider referral processing engine 100 are identified. A referring provider count 302 provides, for an identified provider, a total quantity of issued referrals attributed to the identified provider. Moreover, a drill down feature of the referring provider count 302 renders a listing of all providers to which referrals by the identified provider are attributed, and the quantity of referrals on an individually listed provider basis.

A referred provider count 304 provides, for an identified provider, a total quantity of received referrals attributed to the identified provider. Moreover, a drill down feature of the referred provider count 304 renders a listing of all providers from which received referrals by the identified provider are attributed, and the quantity of referrals on an individually listed provider basis.

A specialties 306 provides, for an identified provider, a primary specialty and a secondary specialty. The specialties 306 is a helper function used to extract specialties information for identified medical service providers to facilitate specialties-based aggregation and analysis of referrals data by other functions identified herein.

A geographic areas 310 provides, for an identified provider, a quantity of referrals received by other providers within a specified geographic area based upon business addresses (obtained from the medical service providers database 104) of referring providers. Such geographic regions can be identified, for example, by neighborhood, zip code, city, county, state, etc.

The various locations of referral sources, for purposes of assigning a geographic area to the identifier provider, may be weighted based upon the quantity of referrals associated with the referring/referred provider. Additionally, the referrals issued by the identified provider to other providers in the specified geographic area can be accumulated and presented.

A referrals score 320 provides, for an identified provider, a referral rating score used by the information retrieval engine 103 and information site 108 to render an overall score for an identified provider. The referral rating score is potentially calculated in a variety of ways including: quantity of referrals received, ratings of providers issuing the received referrals, a combination of the quantity of referrals from providers and ratings of the providers from which the received referrals were issued, etc. The information retrieval engine 103 and information site 108, in turn, assign a weight to the provided referral rating score before applying the referral rating score to a set of other determining factors to compute an overall provider rating score.

A referral rankings 322 generates a ranked listing of N (N being designated by default or user customization) entities (e.g., a provider, a group practice, a hospital, etc.) based upon the provider referral quantities described previously herein above. In general, for any entity for which a referral quantity (to/from) can be calculated, a set of quantity values can be calculated for a set of initially determined entities. Thereafter the results can be ranked and passed to the information retrieval engine 103 and displayed via the information site 108 based upon the quantities. Examples of such ranked output includes a top "N" referred:

- providers by specified geographic area;
- providers by specified specialty;
- group practices by summing referrals of individual providers identified as belonging to a group practice
- providers in conjunction with display of any associated award recognitions;
- providers presented by and/or with hospital affiliation and corresponding hospital ranking;
- providers presented with and associated Overall Patient Rating;
- providers presented along with any supported rating attribute(s) (one or combination of multiple weighted attribute score/rating);
- providers accompanied by reported patient wait times;
- providers accompanied by an overall quality score, that may be based, in part, upon quantity/quality of received referrals.

The referral rankings 322 is also configured to find a ranking of providers by any one, or a combination of, rated attribute(s) and present the results in defined quartiles or any statistical specification/grouping including, for example by specifying a median, mean, average, standard deviation from mean, etc. Multiple ranking types can be used to define primary, secondary, tertiary, etc. ranking criterions having associated weightings. The composite rankings are then used to render an overall ranking based upon rated ranked attributes.

The described medical service provider referral processing engine 100 incorporates a highly extensible, modular, architecture that supports defining and incorporating new functions (add-on functions) meeting needs of a particular application/use. The add-on functions leverage basic referrals data extraction/aggregation functions and the ability to link such extracted/aggregated referrals data to additional data associated with identified medical service providers maintained in the medical service provider database 104. A unique provider connections 324 is an example of such an "add-on" to the referral processing engine 100. The unique provider connections 324 accumulates and provides a listing of unique sources of referrals and/or unique targets of referrals. The unique provider connections 324, like the specialties 306, is a helper function that provides a set of identified referral-based "connections" between medical service providers. Such connections are utilized, for example, by a Trusted circle of providers 328 function described herein below.

A unique geographic connections 326 is another example an "add-on" function on the referral processing engine 100. The unique geographic connections 326 accumulates and presents a listing of unique geographic areas from which referrals have been received or to which referrals have been directed. The add-on functions discussed herein are intended to be exemplary in nature. Other add-ons are contemplated to extend the functionality of the generalized architecture presented herein that integrates medical service provider referral data with other information maintained for such providers in the medical service provider database 104.

A trusted circle of providers 328 analyzes the medical service provider referral data 102, for a specified provider (seed) and related (referred) providers, to render enhanced information, in the form of referral patterns between closely linked providers, displayable as a directed graph. See e.g., FIG. 4. A trusted circle of providers graph depicts a group of providers who are related to one another at least by a common source (the designated seed provider) of at least one referral. In FIG. 4, a primary care provider (PCP) 400 is the designated seed provider. The example provided in FIG. 4 is a very simple example of such a graphical representation of provider referral connections for a trusted circle of providers. The displayed directed graph, representing a trusted circle of providers, provides a basis for rendering a set of referral strength values for a set of immediate referral entities (IRs 405*a-f*) of a specified "seed" provider entity (PCP 400). Any medical service provider entity can be designated as the "seed" for generation of a trusted circle of providers graph.

With continued reference to FIG. 4, the trusted circle of providers graph is separated into two generalized areas. An immediate referral circle 410 area of the depicted graph contains the PCP 400 (seed provider). The immediate referral circle 410 area also includes the immediate referral entities (IR 405(*a-f*)) that correspond to medical service providers that have received at least one referral from the PCP 400 (seed provider). An external referrals area 420 outside the immediate referral circle 410 identifies external referral source entities (ER) 425(*a-e*). The ERs 425(*a-e*) correspond to provider entities that have issued at least one referral to at least one of the IRs 405(*a-f*), but ERs 425 have not received any referrals from the PCP 400 "seed" provider entity. Thus, the illustrative example of FIG. 4 visually depicts the referral relationships (including strengths—indicated by thickness of the connecting arrow) between the primary care provider 400, chosen as the seed medical service provider element, and a set of providers constituting immediate referrals (IR) 405(*a-f*).

The illustrative example of a trusted circle of providers graph in FIG. 4 includes three distinct types of referrals arrows. A "direct referrals" arrow indicates referrals from a seed provider to an IR (e.g. between PCP 400 and IR 405(*a*)). An "indirect referrals" arrow indicates referrals between IRs (e.g. between IR 405(*f*) and IR 405(*d*)). An "outside referrals" arrow indicates referrals from an ER to an IR (e.g. between ER 425(*b*) and IR 405(*c*)). The thickness of the various referral arrows corresponds to a relative quantity of referrals between a source and recipient of the referrals. Thus, the arrow from the primary care provider 400 to the IR 405(*c*) is depicted substantially thicker than other lines to reflect a substantially larger number of referrals by the primary care provider 400 to the IR 405(*c*). Calculations of relative received referral strength of IRs 405(*a-f*), by the Trusted circle of providers 328, based upon data acquired from the provider database 104 and the medical service provider referral data 102, are discussed herein below.

Two types of trusted circles of providers are described herein—"Core Network Referrals" and "Extended Network Referrals" circles of trusted providers. A "Core Network Referrals" trusted circle of providers includes limits calculation of received referral strength to immediate referral entities (i.e. provider entities that have received a referral directly from the "seed" provider (e.g., PCP 400). The calculations of referral strengths for providers are potentially limited to referrals based upon a particular specialty of interest to a user/patient. In such case, referral strengths are potentially calculated from custom/specific provider lists based on a user provider's past referring behavior of a specific specialty or condition. In a particular example, the Core Network Referrals referral strength calculations contain only IRs 405 that remain after applying a specialty or practice area filter. More specifically, the filtered set is determined, for example, based upon a listing limited to providers that were previously visited by the user for a particular specified condition.

An example of the Core Network Referrals begins with a user "X" designating a primary care provider, Dr. Jones. The user X designates heart disease as the particular condition of interest. Thereafter, the provider referral engine 100 generates a core referrals set/graph representing the referrals of Dr. Jones for cardiologists. The results of the Core Network Referrals operation returned by the provider referral engine 100 include a listing of cardiologists for which Dr. Jones issued a referral. The results may be ranked according to the quantity of referrals attributable to the referred cardiologist. Other rank orders are supported by the information retrieval engine 103 and information site 108. Other potentially returned information includes a total number of referrals received by the listed/referred provider, quality scores, ratings, etc. The above example is only one type of potential filtered search carried out by the Core Network Referrals operation. Other filtered referral sets are defined in other cases by any other searchable parameter.

An "Extended Network Referrals" circle of providers expands the population of providers for which a referral strength is calculated. The "Core Network Referrals" includes only first level providers (i.e. providers that received at least one referral from the seed provider). However, "Extended Network Referrals" include, based upon the specified level, additional providers identified by treating each IR at the preceding level (e.g. IRs 405*a-f*) as "seeds" in the next level. Thus a "level 2 Expanded Network Referrals" would add each provider receiving at least one referral from a level 1 IR to the set of IRs for purposes of computing referral strengths of IRs. The number of levels of expansion (referrals of referrals of referrals, etc.) can be increased without bound until a suitable number of providers are identified for purposes of computing referral strengths. The Expanded Network Referrals are intended for use when a filtered set returns an insufficient number of hits using the Core Network Referrals. Thus, in the above case, if Dr. Jones had not referred any patients to cardiologists, then the referrals of medical service providers referred by Dr. Jones are analyzed to identify cardiologists.

The following is an illustrative example of determining/calculating referral strengths for a set of IRs (e.g. IRs 405*a-f* in FIG. 4) using a Core Network Referrals approach to determining relative referral strengths of IR providers. Calculating a referral strength for an individual IR entity within an immediate referrals circle takes into consideration referral counts for each of the three above-described types of referrals (i.e. direct, indirect and outside). In the illustrative example, the referral strength of the IR 405(*c*) is calculated based upon referrals received from: PCP 400 (a substantially larger count indicated by a relatively thick arrow), ER 425(*a*), ER 425(*b*), and IR 405(*b*).

In an illustrative example, the relative referral strengths for IRs 405*a-f* are calculated according to a weighted formula (presented and described below) are utilized in recommendation (e.g. ratings) calculations as well as to present a ranking of IRs (e.g. IRs 405*a-f*) contained within a trusted circle of providers for a designated seed (e.g. PCP 400).

The operation of the trusted circle of providers 328 is integrated with the operation of the provider information retrieval engine 103, by incorporating calculated relative referral strengths for each provider retrieved from the database 104. As such, the referral strengths of providers can be used as a pre-filter or post-filter for searches carried out by the information retrieval engine 103 on the database 104 based upon any searchable parameter type including: geographic areas, specialty, expertise (condition, treatment, disease, disorder), accepted insurance, etc. Other searchable data elements maintained by the database 104 for user filter/comparison/qualifiers may also include the following, as well as others, to build on a recommendation score. Such data includes: patient feedback metrics; affiliated hospitals quality metrics; medical Education metrics; experience metrics; certification metrics.

The trusted circle of providers 328 consumes yet other information to augment bare referral numbers. For example, quality measures (e.g. provider rating scores) are incorporated for the listed referred providers along with their overall referral volume numbers.

The trusted circle of providers 328 can generate a variety of referral scores in accordance with provided referral counting/weighting schemes. Two such examples are provided below for rendering a total referral score for any IR 405 provider (e.g., IR 405(*d*)).

First, if different weights are assigned for direct and indirect referrals by specialty, then the following is used to compute an overall referral score for any single/individual one of the IRs 405*a-f* of the PCP 400:

$$(Wdrs*Ndrpp+SUM(Widrs(i)*Nidrpp))*\log(Npcp)+ \\ SUM(Wors(j)*Norpp)$$

Where:

SUM is the sigma summation function, "i" represents IR nodes (in the illustrative example i runs from 1 to 6 for providers 405(*a-f*), and "j" represents ER nodes (in the illustrative example j runs from 1 to 5 for the providers 425(*a-e*).

"dr"—direct referrals from the PCP to a provider

"idr"—indirect referrals from the within PCP immediately reachable cluster

"or"—circle of friends of PCP "or" (outside referrals)

Weights of edges: Wdr, Widr, Wor

Weights of edges per specialty: Wdrs, Widrs, Wors

Number of direct referrals per physician: Ndrpp

Number of indirect referrals per physician: Nidrpp

Number of outside referrals per physician: Norpp

Number of all nodes within PCP immediately reachable cluster: Npcp

Examples of weights are as follows: Wdr=1; Widr=0.5; and Wor=0.25. Thus, referrals directly from the PCP 400 have greatest weight, referrals between IR 405 (e.g. from 405(*f*) to 405(*d*) have a lower weight, and referrals from external referrals 420 (e.g. ER 425(*d*) to IR 405(*e*)) have yet lower weight.

Second, if a same weight is assigned regardless of specialty, the following is used to compute an overall referral score for any single/individual one of the IRs 405*a-f* of the PCP 400:

$$(Wdr*Ndrpp+Widr*SUM(Nidrpp))*\log(Npcp)+ \\ Wor*SUM(Norpp)$$

In the above illustrative examples, the weights are normalized to a range of 0-1. However, any weighting scheme can be used. Moreover, in yet other cases, where referrals are identifiable by a type of facility from which a referral was issued, weights may be assigned based upon the type of facility from which a referral issued.

All references, including publications, patent applications, and patents, cited herein are hereby incorporated by reference to the same extent as if each reference was individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for rendering requested medical service provider entity information via a medical service provider information retrieval engine configured to access information stored in a medical service provider database containing information relating to service provider entities, the method comprising:

identifying a medical service provider entity for which referrals data enhanced medical service provider information will be rendered for presentation to a requesting user;

accessing, by a medical service provider referral processing engine, medical service provider referral information relating to the medical service provider entity, wherein the referral information specifies a value representing referrals received by the medical service provider entity from other medical service provider entities;

performing, by the referral processing engine, a transformation on the medical service provider referral information obtained during the accessing to render a provider entity received referrals value, wherein the transformation comprises at least summing a plurality of referral values corresponding to referrals received by the medical service provider entity from other medical service provider entities;

incorporating the provider entity received referrals value with medical service provider information obtained by the retrieval engine to render referrals data enhanced medical service provider information; and providing the referrals data enhanced medical service provider information for presentation to a requesting user via an on-line interface.

2. The method of claim 1 wherein the performing a transformation comprises attaching the provider entity received referrals value to a database table entry in the provider database for the identified medical service provider entity.

3. The method of claim 1 wherein the performing a transformation comprises rendering a weighted referrals score for the identified medical service provider entity by performing a summation operation based upon a set of received referrals count values for a circle of trusted provider entities, wherein the set of referrals count values includes:

a seed referrals count value corresponding to received referrals from a seed provider entity, an indirect referrals count corresponding to received referrals from a provider entity that received at least one referral from the seed provider entity, and an external referrals count corresponding to received referrals from a provider entity that has not received a referral from the seed provider entity.

4. The method of claim 3 wherein each of the referrals count types is assignable a distinct weight value.

5. The method of claim 3 wherein referrals by a referring medical service provider entity are identifiable by one of the group consisting of:
- a specialty in the case of an individual, and
- a facility type in the case of a facility.

6. The method of claim 3 wherein the weighted referrals score for the identified medical service provider entity is a function of an indirect referrals weighting value applied to a count of all referrals received, by the identified medical service provider entity, from the medical service provider entity that received at least one referral from the seed provider entity.

7. The method of claim 1 wherein the identified medical service provider entity is an identified facility.

8. The method of claim 1 wherein the incorporating comprises rendering, based upon accumulated referrals data for multiple identified provider entities, a ranking of the multiple identified provider entities.

9. The method of claim 8 wherein the ranking comprises grouping multiple identified provider entities into ranked groups.

10. The method of claim 1 wherein the incorporating comprises rendering, based upon accumulated referrals data, a rating value assigned to the identified provider entity.

11. The method of claim 10 wherein the rating value is a referrals rating score for the identified provider entity.

12. The method of claim 11 further comprising incorporating the referrals rating score into a composite rating generated for the identified provider entity from a combination of ratings factors.

13. The method of claim 1 wherein the incorporating comprises rendering, based upon accumulated referrals data for multiple identified provider entities, a filtered set of the multiple identified provider entities by applying a referrals threshold value to the accumulated referrals data for individual ones of the multiple identified provider entities.

14. A non-transitory computer-readable medium including computer-executable instructions for rendering requested medical service provider entity information via a medical service provider information retrieval engine configured to access information stored in a medical service provider database containing information relating to service provider entities, the computer-executable instructions, when executed by a programmed processor, causing execution of a method comprising:
- identifying a medical service provider entity for which referrals data enhanced medical service provider information will be rendered for presentation to a requesting user;
- accessing, by a medical service provider referral processing engine, medical service provider referral information relating to the medical service provider entity, wherein the referral information specifies a value representing referrals received by the medical service provider entity from other medical service provider entities;
- performing, by the referral processing engine, a transformation on the medical service provider referral information obtained during the accessing to render a provider entity received referrals value, wherein the transformation comprises at least summing a plurality of referral values corresponding to referrals received by the medical service provider entity from other medical service entities;
- incorporating the provider entity received referrals value with medical service provider information obtained by the retrieval engine to render referrals data enhanced medical service provider information; and
- providing the referrals data enhanced medical service provider information for presentation to a requesting user via an on-line interface.

15. The non-transitory computer-readable medium of claim 14 wherein the performing a transformation comprises rendering a weighted referrals score for the identified medical service provider entity by performing a summation operation based upon a set of received referrals count values for a circle of trusted provider entities, wherein the set of referrals count values includes:
- a seed referrals count value corresponding to received referrals from a seed provider entity,
- an indirect referrals count corresponding to received referrals from a provider entity that received at least one referral from the seed provider entity, and
- an external referrals count corresponding to received referrals from a provider entity that has not received a referral from the seed provider entity.

16. The non-transitory computer-readable medium of claim 14 wherein the incorporating comprises rendering, based upon accumulated referrals data for multiple identified provider entities, a ranking of the multiple identified provider entities.

17. The non-transitory computer-readable medium of claim 14 wherein the incorporating comprises rendering, based upon accumulated referrals data, a rating value assigned to the identified provider entity.

18. The non-transitory computer-readable medium of claim 17 wherein the rating value is a referrals rating score for the identified provider entity.

19. The non-transitory computer-readable medium of claim 18 further comprising incorporating the referrals rating score into a composite rating generated for the identified provider entity from a combination of ratings factors.

20. A programmed computer system comprising:
- a processor; and
- a non-transitory computer-readable medium including computer-executable instructions for rendering requested medical service provider entity information via a medical service provider information retrieval engine configured to access information stored in a medical service provider database containing information relating to service provider entities, the computer-executable instructions, when executed by the processor, causing execution of a method comprising:
  - identifying a medical service provider entity for which referrals data enhanced medical service provider information will be rendered for presentation to a requesting user;
  - accessing, by a medical service provider referral processing engine, medical service provider referral information relating to the medical service provider entity, wherein the referral information specifies a value representing referrals received by the medical service provider entity from other medical service provider entities;
  - performing, by the referral processing engine, a transformation on the medical service provider referral information obtained during the accessing to render a provider entity received referrals value, wherein the transformation comprises at least summing a plurality of referral values corresponding to referrals received by the medical service provider entity from other medical service provider entities;

incorporating the provider entity received referrals value with medical service provider information obtained by the retrieval engine to render referrals data enhanced medical service provider information; and providing the referrals data enhanced medical service provider information for presentation to a requesting user via on-line interface.

* * * * *